US011406672B2

(12) United States Patent
Wood et al.

(10) Patent No.: US 11,406,672 B2
(45) Date of Patent: Aug. 9, 2022

(54) PROBIOTIC COMPOSITION AND FEED ADDITIVE

(71) Applicant: Sustainable Community Development, LLC, Kansas City, MO (US)

(72) Inventors: Matthew T. Wood, Kansas City, MO (US); Narin Tipsrisukond, Kansas City, MO (US)

(73) Assignee: SUSTAINABLE COMMUNITY DEVELOPMENT, LLC, Kansas City, MO (US)

( * ) Notice: Subject to any disclaimer, the term of this patent is extended or adjusted under 35 U.S.C. 154(b) by 0 days.

(21) Appl. No.: 16/980,713

(22) PCT Filed: Mar. 14, 2019

(86) PCT No.: PCT/US2019/022179
§ 371 (c)(1),
(2) Date: Sep. 14, 2020

(87) PCT Pub. No.: WO2019/178309
PCT Pub. Date: Sep. 19, 2019

(65) Prior Publication Data
US 2021/0023145 A1 Jan. 28, 2021

Related U.S. Application Data

(60) Provisional application No. 62/642,891, filed on Mar. 14, 2018.

(51) Int. Cl.
*A61K 35/742* (2015.01)
*A61K 35/745* (2015.01)
*A61K 35/747* (2015.01)

(52) U.S. Cl.
CPC .......... *A61K 35/742* (2013.01); *A61K 35/745* (2013.01); *A61K 35/747* (2013.01)

(58) Field of Classification Search
None
See application file for complete search history.

(56) References Cited

U.S. PATENT DOCUMENTS

| | | |
|---|---|---|
| 4,551,164 A | 11/1985 | Tenzer |
| 6,849,256 B1 | 2/2005 | Farmer |
| 8,765,450 B2 | 7/2014 | Mathis |
| 8,790,436 B2 | 7/2014 | Ersek et al. |
| 9,096,836 B2 | 8/2015 | Wood |
| 9,175,258 B2 | 11/2015 | Bywater-Ekegard et al. |
| 9,247,757 B2 | 2/2016 | Schmidt et al. |
| 9,499,448 B2 | 11/2016 | Thorpe et al. |
| 10,494,684 B2 | 12/2019 | Penet et al. |
| 2005/0255092 A1 | 11/2005 | Rehberger et al. |
| 2007/0202088 A1 | 8/2007 | Baltzley |
| 2008/0318777 A1 | 12/2008 | Lin et al. |
| 2009/0297481 A1 * | 12/2009 | Powlen ................ A61K 35/747 424/93.3 |
| 2012/0015806 A1 | 1/2012 | Paikray et al. |
| 2012/0031157 A1 | 2/2012 | Paikray |
| 2012/0064605 A1 | 3/2012 | Lorah et al. |
| 2014/0234279 A1 | 8/2014 | Millan |
| 2014/0328815 A1 | 11/2014 | Ware |
| 2015/0237807 A1 | 8/2015 | Valiquette |
| 2016/0029666 A1 | 2/2016 | Carpenter et al. |
| 2017/0197889 A1 | 7/2017 | Connell |
| 2017/0245503 A1 | 8/2017 | Ashby et al. |
| 2018/0235236 A1 | 8/2018 | Yoon et al. |
| 2018/0255786 A1 | 9/2018 | Bywater-Ekegard |
| 2020/0131096 A1 | 4/2020 | Kanagalingam et al. |
| 2020/0189946 A1 | 6/2020 | Sin et al. |
| 2020/0216797 A1 | 7/2020 | Dyson et al. |
| 2020/0245627 A1 | 8/2020 | Wigley et al. |

* cited by examiner

Primary Examiner — Brian Gangle

(57) ABSTRACT

Probiotic compositions containing a consortium of beneficial lactic acid fermenting microbes, bacteria belonging to the Bacilli family, and yeast are disclosed, and methods of using same as human probiotic for ingestion or as an animal feed additive are disclosed.

7 Claims, No Drawings

PROBIOTIC COMPOSITION AND FEED ADDITIVE

FIELD OF THE INVENTION

The present invention relates to microorganism compositions and methods of using them. In particular, the present invention relates to a microorganism consortia composition including lactic acid microorganisms co-cultured with other Bacilli bacteria and yeast to produce a composition useful in numerous industries including agriculture, food and animal feed and feed additives, health, and as a chemical replacement.

BACKGROUND OF THE INVENTION

Environmental awareness, resource constraints, and general public opinion are increasing the demand for efficient green technologies and products. Such green technologies and products are those that promote sustainability and have minimal impact on the environment. One area that is being exploited to develop green technology and products is the use of microorganisms and their specialized properties. Microorganisms have been used in agriculture, animal health, human health, and waste management. In agriculture, microorganisms are used to enhance composting and soil amendment. In animals and humans beneficial bacteria, known as probiotics, are used to prevent illness caused by harmful bacteria invading the natural flora. In waste management, microorganisms are used to accelerate waste decomposition and degrade odorous compounds.

While the use of microorganisms is being exploited, such use is hindered by stability, storage, and efficiency issues. Accordingly, there is a need to develop microorganism-based technologies and products that are stable under various conditions, maintain high titers of microbes, have an appreciable shelf life, and can be easily used.

SUMMARY OF THE INVENTION

In a first aspect, the invention provides a probiotic composition that is free of detectable non-Bacilli bacteria. In one embodiment, the subject probiotic composition in liquid form contains a carbon source, a fermentation product, about 20,000 to 50,000 cfu/mL of a combination of at least five lactic acid bacteria including *Bacillus subtilis*, a *Lactobacillus* sp., a *Bifidobacterium* sp., a *Lactococcus* sp., and *Streptococcus thermophilus*, at least two non-pathogenic gram-positive Bacilli bacteria capable of fermentation each at a titer of>300,000 cfu/mL, and a yeast.

In another embodiment, the subject probiotic composition is in dry form, obtained by lyophilizing, spray-drying, or the like, a liquid composition containing a carbon source, a fermentation product, about 20,000 to 50,000 cfu/mL of a combination of at least five lactic acid bacteria including *Bacillus subtilis*, a *Lactobacillus* sp., a *Bifidobacterium* sp., a *Lactococcus* sp., and *Streptococcus thermophilus*, at least two non-pathogenic gram-positive Bacilli bacteria capable of fermentation each at a titer of>300,000 cfu/mL, and a yeast.

In another embodiment, the subject probiotic composition in liquid form contains a carbon source, a fermentation product, about 20,000 to 50,000 cfu/mL of a combination of at least five lactic acid bacteria including *Bacillus subtilis*, a *Lactobacillus* sp., a *Bifidobacterium* sp., a *Lactococcus* sp., and *Streptococcus thermophilus*, at least two non-pathogenic gram-positive Bacilli bacteria capable of fermentation each at a titer of>300,000 cfu/mL, a purple non-sulfur bacteria at a titer of at least 50,000 cfu/mL, and a yeast.

In another embodiment, the subject probiotic composition is in dry form, obtained by lyophilizing, spray-drying, or the like, a liquid composition containing a carbon source, a fermentation product, about 20,000 to 50,000 cfu/mL of a combination of at least five lactic acid bacteria including *Bacillus subtilis*, a *Lactobacillus* sp., a *Bifidobacterium* sp., a *Lactococcus* sp., and *Streptococcus thermophilus*, at least two non-pathogenic gram-positive Bacilli bacteria capable of fermentation each at a titer of>300,000 cfu/mL, a purple non-sulfur bacteria at a titer of at least 50,000 cfu/mL, and a yeast.

In one embodiment, the yeast is a species of *Saccharomyces*. In a more specific embodiment, the yeast is *Saccharomyces cerevisiae*. In a still more specific embodiment, the yeast is a specific strain of *Saccharomyces cerevisiae* that is generally recognized as safe for ingestion or approved for use in animal feed or human food, such as e.g., *Saccharomyces cerevisiae* NCYC Sc47, *Saccharomyces cerevisiae* PCM KKP 2059p, or *Saccharomyces cerevisiae* IFO 0203.

In one embodiment, the non-pathogenic gram-positive Bacilli bacteria capable of fermentation is one or more of *Bifidobacterium* spp., *Lactobacillus* spp., *Lactococcus* spp., *Carnobacterium* spp., *Streptococcus* spp., and *Bacillus* spp. In a more specific embodiment, the non-pathogenic gram-positive Bacilli bacteria capable of fermentation is one or more of *Bifidobacterium animalis, Lactobacillus acidophilus, Bacillus subtilus, Lactococcus lactis, Lactobacillus casei, Lactobacillus plantarum, Carnobacterium divergens,* and *Lactobacillus rhamnosus.*

In a particular embodiment, the subject non-pathogenic gram-positive Bacilli bacteria capable of fermentation comprises *Bifidobacterium animalis* DSM 16284, *Lactobacillus acidophilus* CECT 4529, and *Bacillus subtilus* ATCC PTA 6737. In another particular embodiment, the subject non-pathogenic gram-positive Bacilli bacteria capable of fermentation comprises comprises *Lactococcus lactis* PCM B/00039, *Lactobacillus casei* PCM B/00080, *Lactobacillus plantarum* PCM B/00081, and *Carnobacterium divergens* PCM KKP 2012p. In yet another particular embodiment, the subject non-pathogenic gram-positive Bacilli bacteria capable of fermentation comprises comprises *Lactobacillus rhamnosus* ATCC 7469.

In one embodiment, the carbon source contains a carbohydrate, such as glucose, starch, cellulose, fructose, sucrose, or the like. In one embodiment, the carbon source is plant material such as silage. In another embodiment, the carbon source is a plant material from the grass family (Poaceae). In some embodiments, the carbon source is relatively unrefined plant material, such as silage, stover, chaff, grass, stalks, leaves, and the like. In other embodiments, the carbon source comprises a more refined plant material, such as flour, syrup, molasses, or the like. In another embodiment, the carbon source comprises purified or semi-purified organic molecules, such as protein, fat, fatty acids, carbohydrates, or the like. In a more specific embodiment, the carbon source comprises a bran from grain, such as, e.g., rice bran, or a syrup or molasses from sugar cane.

In one embodiment, the fermentation product contains an organic acid, an alcohol, or both. In a particular embodiment, the fermentation product contains lactic acid or ethanol. In another embodiment, fermentation product contains fermented sugar cane molasses or fermented rice bran.

In a specific embodiment, the probiotic composition contains (a) a mixture of live lactic acid bacteria at cumulative titer of 20,000-50,000 cfu/mL including (i) *Bacillus subtilis*, (ii) a *Lactobacillus* sp., (iii) a *Bifidobacterium* sp., (iv) a *Lactococcus* sp., and (v) *Streptococcus thermophilus;* (b) *Saccharomyces cerevisiae* NCYC Sc47; and (c)>300,000 cfu/mL each of (i) *Bifidobacterium animalis* DSM 16284, (ii) *Lactobacillus acidophilus* CECT 4529, and (iii) *Bacillus subtilus* ATCC PTA 6737. In a more specific embodiment, the probiotic composition contains (a) a mixture of live lactic acid bacteria at cumulative titer of 20,000-50,000 cfu/mL including (i) *Bacillus subtilis,* (ii) a *Lactobacillus* sp., (iii) a *Bifidobacterium* sp., (iv) a *Lactococcus* sp., and (v) *Streptococcus thermophilus;* (b) *Saccharomyces cerevisiae* NCYC Sc47; (c)>300,000 cfu/mL each of (i) *Bifidobacterium animalis* DSM 16284, (ii) *Lactobacillus acidophilus* CECT 4529, and (iii) *Bacillus subtilis* ATCC PTA 6737; and (d) fermented molasses.

In another specific embodiment, the probiotic composition contains (a) a mixture of live lactic acid bacteria at cumulative titer of 20,000-50,000 cfu/mL including (i) *Bacillus subtilis,* (ii) a *Lactobacillus* sp., (iii) a *Bifidobacterium* sp., (iv) a *Lactococcus* sp., and (v) *Streptococcus thermophilus;* (b) *Saccharomyces cerevisiae* PCM KKP 2059p; and (c)>300,000 cfu/mL each of (i) *Lactococcus lactis* PCM B/00039, (ii) *Lactobacillus casei* PCM B/00080, (iii) *Lactobacillus plantarum* PCM B/00081, and (iv) *Carnobacterium divergens* PCM KKP 2012p. In a more specific embodiment, the probiotic composition contains (a) a mixture of live lactic acid bacteria at cumulative titer of 20,000-50,000 cfu/mL including (i) *Bacillus subtilis,* (ii) a *Lactobacillus* sp., (iii) a *Bifidobacterium* sp., (iv) a *Lactococcus* sp., and (v) *Streptococcus thermophilus;* (b) *Saccharomyces cerevisiae* PCM KKP 2059p; (c)>300,000 cfu/mL each of (i) *Lactococcus lactis* PCM B/00039, (ii) *Lactobacillus casei* PCM B/00080, (iii) *Lactobacillus plantarum* PCM B/00081, and (iv) *Carnobacterium divergens* PCM KKP 2012p; and (d) fermented molasses.

In yet another specific embodiment, the probiotic composition contains (a) a mixture of live lactic acid bacteria at cumulative titer of 20,000-50,000 cfu/mL including (i) *Bacillus subtilis,* (ii) a *Lactobacillus* sp., (iii) a *Bifidobacterium* sp., (iv) a *Lactococcus* sp., and (v) *Streptococcus thermophilus;* (b) *Saccharomyces cerevisiae* IFO 0203; and (c)>300,000 cfu/mL of *Lactobacillus rhamnosus* ATCC 7469. In a more specific embodiment, the probiotic composition contains (a) a mixture of live lactic acid bacteria at cumulative titer of 20,000-50,000 cfu/mL including (i) *Bacillus subtilis,* (ii) a *Lactobacillus* sp., (iii) a *Bifidobacterium* sp., (iv) a *Lactococcus* sp., and (v) *Streptococcus thermophilus;* (b) *Saccharomyces cerevisiae* IFO 0203; (c)>300,000 cfu/mL of *Lactobacillus rhamnosus* ATCC 7469; and (d) fermented molasses.

In a second aspect, the invention provides a method of manufacturing the probiotic composition of the first aspect of the invention. In one embodiment, the method contains the steps of (a) obtaining a fermented product containing live lactic acid bacteria, and then (b) adding a non-pathogenic gram-positive Bacilli bacterium capable of fermentation and a yeast to the fermented product.

In another embodiment, the method contains the steps of (a) fermenting a first carbon source with a lactic acid bacteria consortium to make a fermented product, and (b) adding a non-pathogenic gram-positive Bacilli bacterium capable of fermentation and a yeast to the fermented product. Optionally, a second carbon source or additional first carbon source may be added as a step (c), and the new mixture allowed to ferment to form additional fermentation product.

In one embodiment, the live lactic acid bacteria or the lactic acid bacteria consortium contains *Bacillus subtilis, Lactobacillus* sp., *Bifidobacterium* sp., *Lactococcus* sp., and *Streptococcus thermophilus.* In one embodiment, the carbon source is or contains glucose, sucrose, fructose, starch, and/or cellulose, and the like. In another embodiment, the carbon source is a plant source, such as silage, chaff, stover, bran, and/or syrup or molasses, and the like. In a preferred embodiment, the carbon source is rice bran or sugar cane molasses, and the fermentation product is fermented molasses or fermented bran containing lactic acid.

In a third aspect, the invention provides an animal feed containing a probiotic composition of the first aspect.

In a fourth aspect, the invention provides a method for producing the animal feed of the third aspect. In one embodiment, the probiotic composition is combined with a nutrition source, such as silage, kibbles, feed grain, and the like.

In a fifth aspect, the invention provides a method for maintaining or improving the health of an animal by feeding the animal the probiotic composition of the first aspect or the animal feed of the third aspect of the invention.

In a sixth aspect, the invention provides a method for maintaining or improving the food quality or food yield of an animal raised for food by feeding the animal the probiotic composition of the first aspect or the animal feed of the third aspect of the invention.

DETAILED DESCRIPTION

In accordance with the present invention, compositions including multiple microorganisms as well as methods of use have been discovered. In particular, it has been discovered that a consortium of microorganisms can be cultured to produce compositions having enhanced stability and shelf-life. Such compositions are useful in the agriculture, food and feed, and health industries, as well as chemical replacement in other industries.

I. Compositions

Compositions useful in this invention include microorganisms and additives. The microorganisms may include species of bacteria and fungi, including yeast and mold species. Suitable microorganisms include those commonly known in the art as phototrophic, lactic acid, probiotic, and sulfide-utilizing microorganisms.

Examples of useful phototrophic, lactic acid, probiotic, Bacilli family members, and sulfide-utilizing microorganisms are found, for example, in Bergey's Manual of Determinative Bacteriology and Bergey's Manual of Systematic Bacteriology. For example, sulfide-utilizing microorganisms include species of Purple Non-sulfur Bacteria, Chromatianeae, Green Sulfur Bacteria, Colorless Sulfur Bacteria, and Filamentous Green Bacteria. Probiotic microorganisms may include *Lactobacillus* genus, *Enterococcus* genus, *Bifidiobacterium* genus, *Bacillus* genus, *Pseudomonas* genus, *Sporolactobacillus* genus, *Micromonospora* genus, *Micrococcus* genus, *Rhodococcus* genus, and *E. coli.* Phototrophic microorganisms may include *Rhodopseudomonas, Rodobactor,* and combinations thereof. For example, phototrophic microorganisms may include *Rhodopseudomonas palustris, R. sphaeroides, Rhodospirillum centenum, R. photometricum, R. rubrum, Rhodopila globiformis, Rhodobacter sphaeroides,* and combinations thereof. Lactic acid microorganisms may include *Lactobacillus, Lactococcus* and combinations thereof. For example, lactic acid microorganisms may include *Lactobacillus casei, L. plantarum, L. acidophilus, L. fermentum, L. brevis, L. lactis, L. reuteri, L.* bulgaricus, L. cellobiosus, L. curvatus, L. delbrukil, L. helbeticus, L. euterii, L. salivarius, L. rhamnosus, L. gaserli, L. jensenii, L. sporogenes, Lactococcus lactis, Streptococcus (Enterococcus) faecium, S. faecalis, S. cremoris, S. diacetylactis, S. intermedius, S. lactis, S. thermophilus, Pediococcus acidilactici, P. cerevisiae (damnosus), P. pentosaceus, P. acidilacticii, Leuconostoc mesenteroides, and combinations thereof. Bacilli microorganisms may include *Bacillus* genus and combinations thereof. For example, Bacilli microorganisms may include *Bacillus licheniformis, B. subtilis, B. toyoi, B. amyloliquefaciens, B. megateriu, B. pumilus, B. coagulans, B. lentus, B. thermophilus, B. laterosporus, B. cereus, B. circulans*, and combinations thereof. *Bifidobacterium* microorganisms may include *Bifidobacterium* genus and combinations thereof. For example, *Bifidobacterium* microorganisms may include *Bifidobacterium bifidum, B. pseudolongum, B. thermophilus, B. adolescentis, B. animalis, B. infantis, B. longum*, and combinations thereof. *Pseudomonas* microorganism may include *Pseudomonas aeruginosa, P. putida, P. cepacia, P. fluorescens*, and combinations thereof.

In some embodiments, the subject probiotic composition contains non-pathogenic gram-positive Bacilli bacteria. In more specific embodiments, the non-pathogenic gram-positive Bacilli bacteria of the subject probiotic composition contains one or more of *Bifidobacterium actinocoloniiforme, Bifidobacterium adolescentis, Bifidobacterium angulatum, Bifidobacterium animalis, Bifidobacterium aquikefiri, Bifidobacterium asteroides, Bifidobacterium biavatii, Bifidobacterium bifidum, Bifidobacterium bohemicum, Bifidobacterium bombi, Bifidobacterium boum, Bifidobacterium breve, Bifidobacterium callitrichos, Bifidobacterium catenulatum, Bifidobacterium choerinum, Bifidobacterium commune, Bifidobacterium coryneforme, Bifidobacterium cuniculi, Bifidobacterium crudilactis, Bifidobacterium denticolens, Bifidobacterium dentium, Bifidobacterium eulemuris, Bifidobacterium faecale, Bifidobacterium gallicum, Bifidobacterium gallinarum, Bifidobacterium hapali, Bifidobacterium indicum, Bifidobacterium inopinatum, Bifidobacterium kashiwanohense, Bifidobacterium infantis, Bifidobacterium lemurum, Bifidobacterium longum, Bifidobacterium magnum, Bifidobacterium merycicum, Bifidobacterium minimum, Bifidobacterium mongoliense, Bifidobacterium moukalabense, Bifidobacterium myosotis, Bifidobacterium pseudocatenulatum, Bifidobacterium pseudolongum, Bifidobacterium psychraerophilum, Bifidobacterium pullorum, Bifidobacterium reuteri, Bifidobacterium ruminantium, Bifidobacterium saguini, Bifidobacterium scardovii, Bifidobacterium stellenboschense, Bifidobacterium stercoris, Bifidobacterium saeculare, Bifidobacterium subtile, Bifidobacterium thermacidophilum, Bifidobacterium thermophilum, Bifidobacterium tissieri*, and *Bifidobacterium tsurumiense, Bifidobacterium animalis* ssp. *animalis* (DSM 16284), *Bifidobacterium longum* subsp. *Suis* (DSM 20211), *Bifidobacterium animalis* subsp. *animalis* (DSM 20104), *Bifidobacterium animalis* subsp. *lactis* (DSM 20105), and *Bifidobacterium animalis* subsp. *lactis* (ATCC 27536), *Lactobacillus acetotolerans, Lactobacillus acidifarinae, Lactobacillus acidipiscis, Lactobacillus acidophilus, Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustorum, Lactobacillus curvatus, Lactobacillus delbrueckii* subsp. *bulgaricus, Lactobacillus delbrueckii* subsp. *delbrueckii, Lactobacillus delbrueckii* sub sp. *lactis, Lactobacillus dextrinicus, Lactobacillus dioliovorans, Lactobacillus equi, Lactobacillus equigenerosi, Lactobacillus farraginis, Lactobacillus farciminis, Lactobacillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus hammesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefiranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracasei, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus protectus, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae*, and *Lactobacillus zymae, Lactobacillus casei* DSM 28872, *Lactobacillus casei* PCM B/00080 , *Lactobacillus casei* DSM 28872, *Lactobacillus plantarum* KKP/593/p, *Lactobacillus plantarum* KKP/788/p, *Lactobacillus plantarum* PCM B/00081, *Lactobacillus plantarum* (NCIMB 41638), *Lactobacillus plantarum* DSM 29024, *Lactobacillus plantarum* (ATCC 55943), *Lactobacillus plantarum* (ATCC 55944), *Lactobacillus plantarum* (ATCC PTSA-6139), *Lactobacillus plantarum* (CNCM I-3235), *Lactobacillus plantarum* DSM 11672, *Lactobacillus plantarum* (DSM 12836), *Lactobacillus plantarum* (DSM 12837), *Lactobacillus plantarum* (DSM 16565), *Lactobacillus plantarum* (DSM 16568), *Lactobacillus plantarum* (DSM 18112), *Lactobacillus plantarum* (DSM 18113), *Lactobacillus plantarum* (DSM 18114), *Lactobacillus plantarum* (DSM 19457), *Lactobacillus plantarum* (DSM 21762), *Lactobacillus plantarum* (DSM 23375), *Lactobacillus plantarum* (DSM 29025), *Lactobacillus plantarum* (DSM 3676), *Lactobacillus plantarum* (DSM 3677), *Lactobacillus plantarum* (DSM 8862), *Lactobacillus plantarum* (DSM 8866), *Lactobacillus plantarum* (LMG-21295), *Lactobacillus plantarum* (NCIMB 30083), *Lactobacillus plantarum* (NCIMB 30084), *Lactobacillus plantarum* (NCIMB 30084), *Lactobacillus plantarum* (NCIMB 30084), *Lactobacillus* plantarum (NCIMB 30236), *Lactobacillus plantarum* (NCIMB 41028), *Lactobacillus plantarum* (NCIMB 42150), *Lactobacillus plantarum* (VTT E-78076), *Lactobacillus plantarum C* KKP/788/p, *Lactobacillus plantarum* CECT 4528, *Lactobacillus plantarum* CECT 4528, *Lactobacillus plantarum K* KKP/593/p, *Lactobacillus plantarum* LP287, *Lactobacillus plantarum* LP329, *Lactobacillus plantarum* LP329, *Lactobacillus plantarum* NCIMB 30238, *Lactobacillus buchneri* KKP/907/p, *Lactobacillus buchneri* (DSM 22963), *Lactobacillus buchneri* (DSM 12856) , *Lactobacillus buchneri* (DSM 13573), *Lactobacillus buchneri* CCM 1819, *Lactobacillus buchneri* (DSM 16774), *Lactobacillus buchneri* DSM 22501, *Lactobacillus buchneri* LN 40177 , *Lactobacillus buchneri* LN4637, *Lactobacillus buchneri* LN 40177, *Lactobacillus buchneri* NCIMB 40788, *Lactobacillus acidophilus* CECT 4529, *Lactobacillus acidophilus* NBIMCC 8242, *Lactobacillus rhamnosus* (NCIMB 41640), *Lactobacillus rhamnosus* (NCIMB 30121), *Lactobacillus rhamnosus* DSM 29226, *Lactobacillus rhamnosus* DSM 7133, *Lactobacillus rhamnosus* (CNCM-I-3698), *Lactobacillus rhamnosus* ATCC 7469, *Lactobacillus fermentum* (NCIMB 41636), *Lactobacillus brevis* (DSM 12835) , *Lactobacillus brevis* (DSM 21982), *Lactobacillus brevis* (DSM 12835), *Lactobacillus brevis* DSMZ 16680, *Lactobacillus paracasei* (DSM 16245), *Lactobacillus paracasei* (DSM 16773), and *Lactobacillus paracasei* NCIMB 30151, *Lactococcus chungangensis, Lactococcus formosensis, Lactococcus fujiensis, Lactococcus garvieae, Lactococcus hircilactis, Lactococcus lactis, Lactococcus laudensis, Lactococcus nasutitermitis, Lactococcus piscium, Lactococcus plantarum, Lactococcus raffinolactis, and Lactococcus taiwanensis, Lactococcus lactis* PCM B/00039, *Lactococcus lactis* (DSM 11037), *Lactococcus lactis* (NCIMB 30117), and *Lactococcus lactis* (NCIMB 30160), *Bacillus subtilis, Bacillus licheniformis,* and *Bacillus amyloliquefaciens, Bacillus subtilis* (DSM 5750), *Bacillus subtilis* C-3102 (DSM 15544), *Bacillus subtilis* (ATCC PTA-6737), *Bacillus subtilis* (LMG S-15136, *Bacillus subtilis* (DSM 28343), *Bacillus subtilis* (DSM 27273), *Bacillus subtilis* DS098, *Bacillus subtilis* MBS-BS-01, *Bacillus subtilis* (ATCC 2107), *Bacillus subtilis* DSM 17299, *Bacillus subtilis* (CBS 117162), *Bacillus licheniformis* (DSM 5749), *Bacillus licheniformis* DSM 28710, *Bacillus licheniformis* (DSM 19670), *Bacillus licheniformis* (DSM 21564), *Bacillus licheniformis* ATCC 53757, *Bacillus amyloliquefaciens* CECT 5940, *Bacillus amyloliquefaciens* (DSM 9553), *Bacillus amyloliquefaciens* (DSM 9554), *Bacillus amyloliquefaciens* (PTA-6507), *Bacillus amyloliquefaciens* (NRRL B-50013), *Bacillus amyloliquefaciens* (NRRL B-50104), *Bacillus amyloliquefaciens* SD80, and *Bacillus amyloliquefaciens* (ATCC 3978), *Carnobacterium alterfunditum, Carnobacterium divergens, Carnobacterium funditum, Carnobacterium gallinarum, Carnobacterium iners, Carnobacterium inhibens, Carnobacterium jeotgali, Carnobacterium maltaromaticum, Carnobacterium mobile, Carnobacterium piscicola, Carnobacterium pleistocenium,* and *Carnobacterium viridans, Carnobacterium divergens* PCM KKP 2012p, *Streptococcus thermophilus,* and *Streptococcus thermophilus* NBIMCC 8253, *Streptococcus thermophilus* CNRZ1066, *Streptococcus thermophilus* LMG13811, *Enterococcus faecium, Enterococcus faecalis, Enterococcus faecium* CECT 4515, *Enterococcus faecium* CCM 6226, *Enterococcus faecium* CNCM I-3236, *Enterococcus faecium* DSM 22502, *Enterococcus faecium* NCIMB 10415, *Enterococcus faecium* SF202, *Enterococcus faecium* SF301, *Enterococcus faecium* DSM 7134, *Enterococcus faecium* DSM 10663, *Enterococcus faecium* NCIMB 11181, *Enterococcus faecium* DSM 21913, and/or *Enterococcus faecium* NBIMCC 8270.

In some embodiments, the subject probiotic composition contains a yeast microorganism. Yeast microorganisms include genera and species within the *Ascomycota phylum*, including true yeasts and fission yeasts. Preferred yeast microorganisms may include *Saccharomyces* genus and combinations thereof. Examples of useful yeast include for example *Saccharomyces cerevisiae*. In one embodiment, a subject probiotic composition contains a *Saccharomyces cerevisiae*. In a more specific embodiment, the subject yeast is *Saccharomyces cerevisiae* CNCM I-3060, *Saccharomyces cerevisiae* NCYC R397, *Saccharomyces cerevisiae* CNCM I-3399, *Saccharomyces cerevisiae* NCYC R646, *Saccharomyces cerevisiae* CBS 493.9, *Saccharomyces cerevisiae* CNCM I-1077, *Saccharomyces cerevisiae* NCYC Sc 47, *Saccharomyces cerevisiae* CNCM I-4407, *Saccharomyces cerevisiae* MUCL 39885, *Saccharomyces cerevisiae* NCYC R404, *Saccharomyces cerevisiae* NCYC R404, *Saccharomyces cerevisiae* PCM KKP 2059p, or *Saccharomyces cerevisiae* CNCM I-1079.

Preferably, at least one microorganism is included in the compositions of the invention. More preferably, the compositions include consortiums of two or more microorganisms. It is contemplated that where two or more microorganisms form the composition, the microorganisms are co-cultured. The microorganisms may be propagated by methods known in the art. For example, the microorganisms may be propagated in a liquid medium under anaerobic or aerobic conditions. Suitable liquid mediums used for growing microorganism include those known in the art.

In one embodiment, the composition includes a total number of microorganisms of about 1 to about 1 million colony forming units (CFU) per milliliter. Preferably, the composition includes a total number of microorganisms of about 100,000 to about 800,000 CFU per milliliter. More preferably, the composition includes a total number of microorganisms of about 250,000 to about 600,000 CFU per milliliter. Most preferably, the composition includes a total number of microorganisms of about 300,000 CFU per milliliter.

In one embodiment, the probiotic composition contains a first mixture of live lactic acid bacteria cultures at a collective "low titer", and one or more additional non-pathogenic gram-positive bacteria of the Bacilli family that are capable of fermentation at a "high titer" for each additional individual species/strain of bacteria, and a fermenting yeast. By collective titer, what is meant is the individual titers of each of the first live lactic acid bacteria adds up to the collective titer. For example, if the lactic acid bacteria (LAB) consist of 15,000 cfu/mL of a *Bacillus* sp., 12,000 cfu/mL of a *Lactobacillus* sp., and 10,000 cfu/mL of a *Streptococcus* sp., then the collective titer is 37,000 cfu/mL of LAB. In one embodiment, "low titer" is<300,000 cfu/mL, about 0.001-299,999 cfu/mL, about 1,000-250,000 cfu/mL, 5,000-200,000 cfu/mL, 10,000-150,000 cfu/mL, 15,000-100,000 cfu/mL, 20,000-75,000 cfu/mL, 25,000-60,000 cfu/mL, 30,000-55,000 cfu/mL, about 10,000 cfu/mL, about 11,000 cfu/mL, about 12,000 cfu/mL, about 13,000 cfu/mL, about 14,000 cfu/mL, about 15,000 cfu/mL, about 16,000 cfu/mL, about 17,000 cfu/mL, about 18,000 cfu/mL, about 19,000 cfu/mL, about 20,000 cfu/mL, about 21,000 cfu/mL, about 22,000 cfu/mL, about 23,000 cfu/mL, about 24,000 cfu/mL, about 25,000 cfu/mL, about 30,000 cfu/mL, about 35,000 cfu/mL, about 40,000 cfu/mL, about 45,000 cfu/mL, about 50,000 cfu/mL, about 55,000 cfu/mL, about 60,000 cfu/mL, about 65,000 cfu/mL, about 70,000 cfu/mL, about 75,000 cfu/mL, about 80,000 cfu/mL, about 85,000 cfu/mL, about 90,000 cfu/mL, about 95,000 cfu/mL, about 100,000 cfu/mL, about 105,000 cfu/mL, about 110,000 cfu/mL, about 115,000 cfu/mL, about 120,000 cfu/mL, about 125,000 cfu/mL, about 150,000 cfu/mL, about 175,000 cfu/mL, about 200,000 cfu/mL, about 225,000 cfu/mL, about 250,000 cfu/mL, about 275,000 cfu/mL, or about 299,000 cfu/mL.

In one embodiment, "high titer" is ≥300,000 cfu/mL, 300,000-10,000,000 cfu/mL, 500,000-1,000,000 cfu/mL, about 300,000 cfu/mL, about 325,000 cfu/mL, about 350,000 cfu/mL, about 375,000 cfu/mL, about 400,000 cfu/mL, about 425,000 cfu/mL, about 450,000 cfu/mL, about 475,000 cfu/mL, about 500,000 cfu/mL, about 525,000 cfu/mL, about 550,000 cfu/mL, about 575,000 cfu/mL, about 600,000 cfu/mL, about 625,000 cfu/mL, about 650,000 cfu/mL, about 675,000 cfu/mL, about 700,000 cfu/mL, about 725,000 cfu/mL, about 750,000 cfu/mL, about 775,000 cfu/mL, about 800,000 cfu/mL, about 825,000 cfu/mL, about 850,000 cfu/mL, about 875,000 cfu/mL, about 900,000 cfu/mL, about 925,000 cfu/mL, about 950,000 cfu/mL, about 975,000 cfu/mL, about 1,000,000 cfu/mL, about 1,250,000 cfu/mL, about 1,500,000 cfu/mL, about 1,750,000 cfu/mL, about 2,000,000 cfu/mL, about 2,500,000 cfu/mL, about 3,000,000 cfu/mL, about 3,500,000 cfu/mL, about 4,000,000 cfu/mL, about 4,500,000 cfu/mL, about 5,000,000 cfu/mL, about 5,500,000 cfu/mL, about 6,000,000 cfu/mL, about 6,500,000 cfu/mL, about 7,000,000 cfu/mL, about 7,500,000 cfu/mL, about 8,000,000 cfu/mL, about 8,500,000 cfu/mL, about 9,000,000 cfu/mL, about 9,500,000 cfu/mL, about 10,000,000 cfu/mL, about 1.5E+7, about 2E+7, about 2.5+7, about 3E+7, about 3.5E+7, about 4E+7, about 4.5E+7, about 5E+7, about 5.5E+7, about 6E+7, about 6.52E+7, about 7E+7, about 7.5E+7, about 8E+7, about 8.5E+7, about 9E+7, about 9.5E+7, about 1E+8, about 2E+8, about 3E+8, about 4E+8, about 5E+8, about 6E+8, about 7E+8, about 8E+8, about 9E+8, about 1E+9, about 3E+9, about 4E+9, about 5E+9, about 6E+9, about 7E+9, about 8E+9, about 9E+9, about 1E+10, about 2E+10, about 3E+10, about 4E+10, about 5E+10, about 6E+10, about 7E+10, about 8E+10, about 9E+10, or 1E+11 cfu/mL.

In those embodiments in which the probiotic composition is in a dry form, the liquid probiotic compositions described herein are dried. "Dry form" refers to a composition containing ≤15% water by weight, ≤14% water by weight, ≤13% water by weight, ≤12% water by weight, ≤11% water by weight, ≤10% water by weight, ≤9% water by weight, ≤8% water by weight, ≤7% water by weight, ≤6% water by weight, ≤5% water by weight, ≤4% water by weight, ≤3% water by weight, ≤2% water by weight, ≤1% water by weight, 1%-5% water by weight, 2%-6% water by weight, about 3% water by weight, about 4% water by weight, about 5% water by weight, about 6% water by weight, about 7% water by weight, or about 8% water by weight. In one embodiment, the dry form of the probiotic composition is produced by evaporation, spray-drying, lyophilization, or the like. In some embodiments, the dry probiotic composition is encapsulated or combined with an excipient to promote the stability and viability of the microbes over time and under varying temperature conditions. In some embodiments, the dry probiotic composition is divided into micron scale particles that are subsequently coated with biocompatible polymers, such as polyethylene glycol (PEG), chitin, dextrin, polylactic glycolic acid copolymer (PLGA), polylactic acid (PLA), polyglycolic acid (PGA), or the like.

In one embodiment, the composition includes living and non-living microorganisms. In another embodiment, the composition includes living or non-living microorganisms. Compositions containing non-living microorganisms may contain extracts of the microorganisms. Such extracts may be considered a liquid fermentation product of the living microorganisms. The extracts of microorganisms include, by way of example, enzymes, metabolites, proteins, and other substances that are produced by microorganisms and are capable of eliciting an effect on an environment regardless of the living status of the microorganism.

In one embodiment, the composition is fermented to produce a fermentation product. The composition may be fermented for about 1, 2, 3, 4, 5, 6, 7, 8, 9, 10, 11, 12, 13, 14, 15, 16, 17, 18, 19, 20, 21, 22, 23, 24, 25, or more days. Preferably, the composition is fermented for at least about 15 to about 23 days. More preferably, the composition is fermented for at least 21 days. More preferably, the composition is fermented for at least 15 days.

The compositions may also include additives. Suitable additives include substances known in the art that may support growth, production of specific metabolites by the microorganism, alter pH, enrich for target metabolites, enhance insecticidal effects, and combinations thereof. Exemplary additives include carbon sources, nitrogen sources, inorganic salt, organic acid, growth media, vitamins, minerals, acetic acid, amino acids and the like.

Examples of suitable carbon sources include, without limitation, starch, peptone, yeast extract, amino acids, sugars such as glucose, arabinose, mannose, glucosamine, maltose, sugar cane, molasses, rum, and the like; salts of organic acids such as acetic acid, fumaric acid, adipic acid, propionic acid, citric acid, gluconic acid, malic acid, pyruvic acid, malonic acid and the like; alcohols such as ethanol, glycerol, and the like; oil or fat such as soybean oil, rice bran oil, olive oil, corn oil, and sesame oil. The amount of the carbon source added varies according to the kind of carbon source and is typically between 1 to 100 grams per liter of medium. The weight fraction of the carbon source in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition. Preferably, molasses is contained in the medium as a carbon source, at a concentration of about 2 to 20% (w/v). More preferably, the molasses is at a concentration of about 8 to 12% (w/v).

Examples of suitable nitrogen sources include, without limitation, amino acids, yeast extract, tryptone, beef extract, peptone, potassium nitrate, ammonium nitrate, ammonium chloride, ammonium sulfate, ammonium phosphate, ammonia or combinations thereof. The amount of nitrogen source varies according to the nitrogen source, typically between 0.1 to 30 grams per liter of medium. The weight fraction of the nitrogen source in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

Examples of suitable inorganic salts include, without limitation, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc chloride, cupric sulfate, calcium chloride, sodium chloride, calcium carbonate, sodium carbonate, and combinations thereof. The weight fraction of the inorganic salt in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In one embodiment, the compositions of the present invention may further comprise alcohol. Suitable alcohols include any known in the art including, without limitation, methanol, ethanol, n-propanol, allyl alcohol, n-propanol, isopropanol, sec-propanol, n-butanol, sec-butanol, isobutanol, t-butanol, and tert-amyl-alcohol. The weight fraction of the alcohol in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In another embodiment, the compositions of the present invention may further comprise acetic acid, carboxylic acid, or other organic acids. Suitable organic acids include any known in the art including, without limitation, lactic acid, formic acid, acetic acid, propionic acid, butanoic acid, isobutyric acid, 3-methyl butanoic acid, methyl acetate ethyl acetate, propyl acetate, butyl acetate, isobutyl acetate, and 2-methyl butyl acetate. In one embodiment, the acetic acid is included by using vinegar. The weight fraction of the acetic acid in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In yet another embodiment, the compositions of the present invention may further comprise any insect repellents known in the art. Such insect repellants include, without limitation, N,N-diethyl-m-toluamide (DEET), N,N-diethylbenzamide, menthyl 2-pyrrolidone-5-carboxylate, N-aryl and N-cycloalkyl neo-alkanamides, N-lower alkyl neoalkanamides, nepetalactone and combinations thereof. The compositions may also comprise natural oils known for their insect repellent characteristics. Such natural oils include, without limitation, citronella oil, catnip oil, eucalyptus oil, cypress oil, galbanum oil, tolu, Peru balsams, and combinations thereof. The weight fraction of the insect repellents in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The compositions of the invention may be in liquid or dry form. The composition may comprise an aqueous suspension of components. This aqueous suspension may be provided as a concentrated stock solution which is diluted prior to application or as a diluted solution ready-to-use. Also, the composition may be a wettable powder, granules, dust, pellet or colloidal concentrate. Such dry forms may be formulated to dissolve immediately upon wetting or dissolve in a controlled-release, sustained-release, or other time-dependent manner. Also, the composition may be in a dry form that does not depend upon wetting or dissolving to be effective.

The compositions may additionally be provided in a formulation capable of spray. The spray may be a liquid or an aerosol.

The compositions of the present invention may also be formulated in a nutritional composition (e.g. foodstuff, food additive, dietary supplement, or feed additive). For example, the compositions may be included in food products made using fermentation techniques such as wine, beer, and cheese.

A nutritional composition of the present invention may include any of a variety of nutritional agents, which are well known in the art, including vitamins, minerals, essential and non-essential amino acids, carbohydrates, lipids, foodstuffs, dietary supplements, and the like. Thus, the compositions of the present invention may include fiber, enzymes and other nutrients. Preferred fibers include, but are not limited to: psyllium, rice bran, oat bran, corn bran, wheat bran, fruit fiber and the like. Dietary or supplementary enzymes such as lactase, amylase, glucanase, catalase and the like can also be included. Vitamins for use in the compositions of the present invention include vitamins B, C, D, E, folic acid, K, niacin, and the like. Typical vitamins are those, recommended for daily consumption and in the recommended daily amount (RDA).

The compositions of the present invention may be formulated in a pharmaceutical composition, where it is mixed with a pharmaceutically acceptable carrier for any type of administration route, selected according to the intended use.

In some embodiments, the combination of the invention may comprise at least one optional excipient. Non-limiting examples of suitable excipients include antioxidants, additives, diluents, binders, fillers, buffering agents, mineral salts, pH modifying agents, disintegrants, dispersing agents, flavoring agents, nutritive agents, oncotic and osmotic agents, stabilizers, preservatives, palatability enhancers and coloring agents. The amount and types of excipients utilized to form the combination may be selected according to known principles of pharmaceutical science.

In one embodiment, the excipient may include at least one diluent. Non-limiting examples of suitable diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, IVIES, Tris buffers or buffered saline salts (e.g., Tris buffered saline or phosphate buffered saline).

In a further embodiment, the excipient may include a disintegrant. Suitable disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants include minerals such as talc or silica; and fats such as vegetable stearin, magnesium stearate or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

The weight fraction of the excipient(s) in the combination may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the combination.

The compositions of the present invention are stable under various conditions as a liquid or dry form. Preferably, the compositions of the present invention are stable at room temperature.

II. Methods

The compositions disclosed herein are useful in agriculture, human and animal health, food and/or feed, and as chemical replacements. The present invention encompasses methods of benefiting an environment or subject that would benefit from a microorganism composition. The methods may be used to replace chemical compositions, such as insecticides, pesticides, or chemicals. The methods may be used to benefit an environment, such as controlling insect populations, enhancing soil for agriculture purposes, and reducing odor associated with waste. Also, the methods may be used to support or enhance health in a human or animal subject. The methods may be used to treat a subject harboring a condition that would benefit from microorganism-based therapy or that is at risk of developing a condition that would benefit from microorganism-based therapy.

A. Agriculture

The compositions disclosed herein are useful in agriculture methods. Methods of the invention include soil enrichment, plant enrichment, and enhancing biodegradation.

Methods of soil enrichment include applying the composition to the soil to be enriched. The composition may be in liquid or dry form and applied to the soil by methods known in the art. Exemplary methods include spraying, dropping, scattering, and dusting the target soil. Also, the composition may be applied to a water source that feeds the target soil.

In another embodiment, the composition may be used for plant enrichment. Methods of plant enrichment include applying the compositions of the invention to the soil or water source of the plant as described herein. Also, the composition may be added to the water of cut flowers or plants. In another embodiment, seeds may be soaked in a composition of the invention prior to planting. It will be recognized that it may be beneficial to combine any of the methods described herein for soil and plant enrichment.

Addition of a microorganism composition has the effect of enhancing biodegradation of various wastes. Such wastes include, without limitation, food waste, waste produced by humans or animals, and landfill waste. A microorganism composition also has the effect of enhancing composting.

The microorganism composition may be provided either dried or in liquid form to a waste product. The microorganism composition may be provided in a variety of amounts with respect to the weight of the waste product depending on the waste product. In some embodiments, the microorganism composition is provided in an amount ranging from about 0.5 to 50 wt % of the total weight of the waste product. In another embodiment, the microorganism composition is provided in an amount ranging from about 1 to about 3 wt % of the total weight of the waste product. In another embodiment, the amount of microorganism composition provided to the waste is about 2 wt % of the total amount of waste.

The microorganism may be provided in either dry form, liquid form or through the spray. Methods of treating waste products include without limitation, spraying, dusting, sprinkling, liquid inoculation, misting, fumigating, aerosolizing, and other methods known in the art.

B. Health

Methods of the invention include administering compositions to recipient subjects to support and promote health. Methods of the invention include administering compositions to recipient subjects to treat conditions including gastrointestinal and extraintestinal conditions.

Examples of gastrointestinal conditions include, without limitation, acute diarrhea, traveler's diarrhea, lactose intolerance, HIV-associated diarrhea, sucrose isomaltase deficiency, inflammatory bowel disease, pouchitis, carcinogenesis, enteral feeding associated diarrhea, antibiotic associated diarrhea, small bowel bacterial overgrowth, irritable bowel syndrome and conditions associated with enteropathogens. Such enteropathogens include, without limitation, *Helicobacter pylori, Campylobacter jejuni, Campylobacter coli, Staphylococcus aureus, Staphylococcus epidermidis, Streptococcus pyogenes, Streptococcus pneumoniae, Enterococcus faecalis, Haemophilus influenzae, Escherichia coli, Klebsiella pneumoniae, Enterobacter cloacae, Citrobacter freundii, Serratia marcescens,*

*Pseudomonas aeruginosa* and *Pseudomonas maltophilia, Salmonella* sp., *Gasterophilus* sp., *Habronema* sp., *Crascia* sp., *Trichostrongvlus* sp., *Parascaris* sp., *Stroncrulus* sp., *Triodontophorus* sp., *Oxvuris* sp., *Stroncivloides* sp., *Anonlocephala* sp., *Paranonlocephala* sp., *Haemonchus* sp., *Hvostroncmulus* sp., *Spirocerca* sp., *Physoloptera* sp., viruses such as rotavirus, fungi such as *Candida albicans* and *Aspergillus fumigatus,* other species known or found to be associated with gastrointestinal conditions, and combinations of these species. Also contemplated are pathogens known in the art to cause gastrointestinal conditions such as those described in "Merck's Veterinary Manual" by Cynthia M. Kahn or "The Merck Manual of Diagnosis and Therapy" by Mark H. Beers, both incorporated herein by reference.

Also contemplated, is the use of microorganism compositions to treat extraintestinal conditions. Without being bound to a theory, extraintestinal conditions may be treated with microorganisms, microorganism extracts, or microorganism products that can stimulate multiple defense mechanisms including promotion of a nonimmunologic gut defense barrier. This barrier may inhibit translocation of potential pathogens and thus prevent infections of the blood stream and other tissues or organs. Another defense mechanism includes enhancing the intestine's immunologic barrier.

Examples of extraintestinal conditions include, without limitation, appendicitis, autoimmune disorders, multiple sclerosis, Alzheimer's disease, rheumatoid arthritis, celiac disease, diabetes mellitus, organ transplantation, periodontal disease, urogenital diseases (vaginal, urethral and perineal), sexually transmitted disease, HIV infection, HIV replication, surgical associated trauma, surgical-induced metastatic disease, sepsis, weight loss, anorexia, fever control, cachexia, wound healing, ulcers, gut barrier function, allergy, asthma, respiratory disorders, rhinovirus-associated diseases, otitis media, sinusitis, pulmonary disease, circulatory disorders, coronary heart disease, anemia, disorders of the blood coagulation system, renal disease, disorders of the central nervous system, hepatic diseases, constipation, ischaemia, nutritional disorders, osteoporosis, endocrine disorder, epidermal disorders, psoriasis, anthrax, and acne, as well as other conditions known in the art or yet to be discovered that may benefit from treatment with microorganisms, microorganism extracts, or microorganism products.

In use, the microorganism composition may be implemented in a number of different ways depending in part on the targeted subjects and goal of application. A liquid solution containing a microorganism composition may simply be applied directly in the subject's mouth or onto food or beverage the subject will consume. For example, an exemplary liquid spray formulation containing a microorganism composition may be sprayed, for example, on the subject's food prior to consumption.

It should be understood that the microorganism mixture used may be provided in the form of pure concentrate (100% concentration) or a diluted composition with additional excipients in the dosage form (i.e. the amount of active ingredient in the composition is less than or equal to 99.99%, and the remainder consists of inactive excipients). If diluted, the amount of microorganism composition dispensed in the various dosage forms may range from about 1 to 30%, more preferably between about 4 to 8%. One of skill in the art will appreciate that the volume of active component added to the composition will need to be adjusted to account for the dilution and to ensure the end composition comprises the appropriate final concentration of microorganism composition. One of skill in the art will also appreciate that the various components of the composition may be provided in a variety of dosage forms including, but not limited to liquid solution or suspension, emulsion, aerosol, slow release matrices, and the like.

Typical concentration range of microorganisms administered is 1E+3 to 1E+13 cells per day. Preferably, at least about 1E+6, at least about 1E+7, at least about 1E+8 cells per day are administered. However, it will be appreciated that the number of bacteria to be administered will vary according to a number of parameters including subject's size, type of disorder and severity of symptoms.

C. Food

Methods of the invention include using compositions in the preparation of foods that require fermentation. Suitable foods include those known in the art such as beer, wine, cider, dough-based products, breads, and dairy products. Also contemplated are methods using compositions for preservation techniques.

The microorganism composition can be provided to fermentable foods along with fermentation microorganisms. In some embodiments, the microorganism composition may replace the microorganisms typically used in fermentation, in other embodiments they add to the effect of the fermentation microorganisms.

The amount of microorganism composition added to the food product will vary depending on the food product, in some embodiments, the microorganism composition is provided as a dry powder and in other embodiments the microorganism composition is provided as a liquid. Dry formulations of the compositions may be from about 1% to about 99% or more by weight of the composition, while liquid formulations may generally comprise from about 1% to about 99% or more of the microorganism composition by weight.

D. Animal Feed

In one aspect, the invention provides a dietary adjunct containing a probiotic composition, useful for treating and/or preventing disorders and improving feed efficiency and gut microflora in livestock (e.g., cattle, sheep and goats, pigs, and the like), and poultry (e.g., chickens, turkeys, ducks, and the like). The subject probiotic composition can be used as an animal feed additive, or as a direct product to be fed to animals. In one embodiment, the probiotic composition containing live cultures is added directly to animal feed or water. In another embodiment, the probiotic composition is delivered to the animal as a pellet or bolus. In yet another embodiment, the probiotic composition is formulated with an excipient that stabilizes, coats, or otherwise extends the life of the live bacteria and yeast. In one embodiment, the probiotic feed formulation contains the subject probiotic composition combined with an animal chow, feed corn, soybeans, bran, corn gluten meal, mineral composite, calcium powder, leaf powder, alfalfa meal, and/or salt and the like.

E. Chemical Replacement

Methods of the invention include using compositions in place of chemicals. Because the compositions of the present invention are uniquely suited for use in a wide variety of chemical-replacement applications such as for insecticides, pesticides, and cleaning solutions, a wide variety of chemicals may be replaced by use of the invention and such replacements are incorporated therein.

1. Vector Control

The microorganism compositions disclosed herein are particularly useful as insecticides for topical or systemic application to an environment. Such environments include, without limitation, field crops, grasses, fruits and vegetables, lawns, trees, ornamental plants, sand, humans, animals, and other environments that may benefit from insecticide application. The compositions may be formulated for preventative or prophylactic application to an area, and may in certain circumstances be applied to pets, livestock, animal bedding, humans, or in and around farm equipment, barns, domiciles, agricultural facilities, industrial facilities, and other areas that would benefit from insecticide application.

The microorganism compositions are applied to an area or environment of the target insect by conventional methods. Such methods include, without limitation, spraying, dusting, sprinkling, soil soaking, soil injection, seed coating, seedling coating, foliar spraying, aerating, misting, atomizing, fumigating, aerosolizing, and other methods known in the art.

The microorganism compositions may be used in consecutive or simultaneous application to an environmental site alone or in combination with one or more additional insecticides, pesticides, chemicals, fertilizers, or other compounds. The compositions may also be used in conjunction with other treatments such as fertilizers, weed killers, cryoprotectants, surfactants, detergents, insecticidal soaps, dormant oils, polymers, time-release or biodegradable carrier formulations that permit long-term dosing of a target area following a single application of the formulation. Likewise, the formulations may be prepared into edible "baits" or fashioned into insect "traps" to permit feeding or ingestion by a target insect.

An insect as repelled by the composition of this invention includes any member of a large group of invertebrate animals characterized, in the adult state (non-adult insect states include larvae and pupae), by division of the body into head, thorax, and abdomen, three pairs of legs, and, often, but not always) two pairs of membranous wings. This definition therefore includes but is not limited to a variety of biting insects (e.g., ants, bees, black flies, chiggers, fleas, green head flies, mosquitoes, stable flies, ticks, wasps), wood-boring insects (e.g., termites), noxious insects (e.g., house flies, cockroaches, lice roaches, wood lice), and household pests (e.g., flour and bean beetles, dust mites, moths, silverfish, weevils). The compositions of the present invention are effective insect repellents against a wide spectra of common insect pests, such as those mentioned above and also including biting insects, wood-boring insects, noxious insects, and household pests, most particularly mosquitoes, sand flies, stable flies, and ticks. The invention also includes effectiveness against all stages of invertebrate animals including adult, larvae, and pupae stages.

Regardless of the method of application, the amount of the composition is applied at an insecticidally-effective amount, which will vary depending on such factors as, for example, the specific target insects to be controlled, the specific environment, location, plant, crop, or agricultural site to be treated, the environmental conditions, and the method, rate, concentration, stability, and quantity of application of the composition. The formulations may also vary with respect to climatic conditions, environmental considerations, frequency of application, and severity of insect infestation.

The concentration of insecticidal composition which is used for environmental, systemic, topical, or foliar application will vary widely depending upon the nature of the particular formulation, means of application, environmental conditions, and degree of activity. Typically, the insecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the composition by weight. As such, a variety of formulations are preparable, including those formulations that comprise from about 5% to about 95% or more by weight of the composition mix, including those formulations that comprise from about 10% to about 90% or more by weight of the composition. Naturally, formulations may comprise from about 15% to about 85% or more by weight of the composition, and formulations comprising from about 20% to about 80% or more by weight of the composition are also considered to fall within the scope of the present disclosure.

In compositions in which intact microorganisms are included, preparations will generally contain from about $1E+4$ to about $1E+8$ cells/mg, although in certain embodiments it may be desirable to utilize formulations comprising from about $1E+2$ to about $1E+4$ cells/mg, or when more concentrated formulations are desired, compositions comprising from about $1E+8$ to about $1E+10$ or $1E+11$ cells/mg may also be formulated.

The insecticidal formulation of the invention may be administered to a particular area or environment in one or more applications as needed, with a typical field application rate per hectare ranging on the order of from about 50 g/hectare to about 500 g/hectare of composition, or alternatively, from about 500 g/hectare to about 1000 g/hectare may be utilized. In certain instances, it may even be desirable to apply the composition to a target area at an application rate of from about 1000 g/hectare to about 5000 g/hectare or more of composition. In fact, all application rates in the range of from about 50 g of composition per hectare to about 10,000 g/hectare are contemplated to be useful in the management, control, and killing of target insect pests using such insecticidal formulations. As such, rates of about 100 g/hectare, about 200 g/hectare, about 300 g/hectare, about 400 g/hectare, about 500 g/hectare, about 600 g/hectare, about 700 g/hectare, about 800 g/hectare, about 900 g/hectare, about 1 kg/hectare, about 1.1 kg/hectare, about 1.2 kg/hectare, about 1.3 kg/hectare, about 1.4 kg/hectare, about 1.5 kg/hectare, about 1.6 kg/hectare, about 1.7 kg/hectare, about 1.8 kg/hectare, about 1.9 kg/hectare, about 2.0 kg/hectare, about 2.5 kg/hectare, about 3.0 kg/hectare, about 3.5 kg/hectare, about 4.0 kg/hectare, about 4.5 kg/hectare, about 6.0 kg/hectare, about 7.0 kg/hectare, about 8.0 kg/hectare, about 8.5 kg/hectare, about 9.0 kg/hectare, and even up to and including about 10.0 kg/hectare or greater of composition may be utilized in certain agricultural, industrial, and domestic applications of the insecticidal formulations described herein.

2. Cleaning Solutions

Cleaning solutions that use the compositions of the invention are contemplated. In particular, cleaning solutions that replace all or part of the chemical component typically included in cleaning solutions are contemplated. Methods of cleaning include contacting a surface to be cleansed with a composition of the invention. The methods of the invention may be used to control odor, control disease causing pathogens, and break down sludge, scum, dirt, grease, and grime. In another embodiment, a composition of the invention may be added to water to clean the water of impurities. The compositions of the invention may be used in cleaning solutions used to clean a variety of surfaces. Such surfaces include all washable surfaces and all hard surfaces, including plastic, fiberglass, wood, concrete, synthetic materials, composite materials, vegetation, fruits, vegetables, and others known in the art. Cleaning solutions including compositions of the present invention may also be used to clean water (i.e. ponds, lakes, rivers, aquariums, pools, etc.), septic tanks, holding tanks, and lagoons.

Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

The term "about" means within the inclusive range of±15% of the numerical value it modifies.

As used herein, "administering" is used in its broadest sense to mean contacting a subject, surface, liquid, or environment with a composition of the invention.

The term "co-culture" refers to a culture of microorganisms that includes at least two microorganisms of the present invention, described herein.

The term "insecticidally-effective amount" refers to an amount of the composition that can bring about death to at least one insect, or to noticeably reduce insect growth, feeding, or normal physiological development. This amount will vary depending on such factors as, for example, the specific target insects to be controlled, the specific environment, location, plant, crop, or agricultural site to be treated, the environmental conditions, and the method, rate, concentration, stability, and quantity of application. The formulations may also vary with respect to climatic conditions, environmental considerations, frequency of application, and severity of insect infestation.

The term "detectable" as used herein means at or above the limit of detection of a colony-forming unit of particular bacteria, yeast, or other microbes in a probiotic composition. Methods for determining the presence of (detecting) a particular species or strain of microbe include culture techniques and non-culture techniques. Culture techniques include the use of selective agar media and determination of colony morphology, such as e.g., LAMVAB and Rogosa agar for *Lactobacilli* ssp., liver-cysteine-lactose and raffinose for *Bifidobacterium* ssp., heterotrophic plate counting, and the like. Non-culture techniques include e.g., flow cytometry, direct epifluorescent counting, PCR and other DNA-based methods, such as quantitative PCR, and metabolic/chemical methods, such as propridium monoazide PCR or ethidium monoazide PCR. Methods of detection useful in the practice of this invention are described in Catherine Davis, "Enumeration of probiotic strains: Review of culture-dependent and alternative techniques to quantify viable bacteria," Journal of Microbiological Methods, Volume 103, 2014, pp. 9-17; Jackson and Bird, "Comparison of two selective media for the detection and enumeration of Lactobacilli in human faeces," Journal of Microbiological Methods 51 (2002) 313-321; Lu et al., "Fine Structure of Tibetan Kefir Grains and Their Yeast Distribution, Diversity, and Shift," PLoS One. 2014; 9(6): e101387; Rachbid et al., "Assessment of the microbial diversity of Brazilian kefir grains by PCR-DGGE and pyrosequencing analysis," Food Microbiology, Volume 31, Issue 2, September 2012, Pages 215-221; Furet et al., "Molecular quantification of lactic acid bacteria in fermented milk products using real-time quantitative PCR," International Journal of Food Microbiology, Volume 97, Issue 2, 15 Dec. 2004, Pages 197-207; and Garćia-Cayuel et al., "Simultaneous detection and enumeration of viable lactic acid bacteria and bifidobacteria in fermented milk by using propidium monoazide and real-time PCR," International Dairy Journal, Volume 19, Issues 6-7, June-July 2009, Pages 405-409.

The phrase "fermentation product" refers to a mixture including at least one microorganism, expression products of the microorganism(s), substances produced by the microorganisms, and extracts of the microorganisms. In some embodiments, the fermentation product is a gas or organic compound product of the fermentation of a carbohydrate, such as an organic acid like acetic acid, citric acid, gluconic acid, lactic acid, propionic acid, pyruvic acid, or succinic acid, a gas like carbon dioxide, or an alcohol like ethanol. In a preferred embodiment, the fermentation product is lactic acid, ethanol, or a combination of lactic acid and ethanol.

Fermentation product refers to both or either organic chemical products of a fermentation reaction (e.g., carbon dioxide, ethanol, lactic acid, propionic acid), and/or the fermented carbon source (e.g., fermented sugar cane molasse, fermented rice bran).

The term "finished product" refers to a mixture including a fermentation product. The finished product may include additional additives.

The phrase "non-pathogenic gram-positive Bacilli bacteria" refers to those bacteria that belong to the Bacilli taxonomic class of bacteria that contains two orders, Bacillales and Lactobacillales. The term "gram-positive" is used herein to distinguish the subject Bacilli from the group of gram-negative rod-shaped bacteria that are sometimes referred to as bacilli, including for example *Escherichia coli* and other coliform bacteria. The term "non-pathogenic" is used to refer to those Bacilli that do not cause disease or harm to a plant or animal, i.e., excluding pathogenic bacteria. For example, certain species of *Bacillus* (e.g., anthraces), *Listeria, Staphylococcus,* and *Streptococcus* are pathogenic and are excluded.

Non-limiting examples of non-pathogenic gram-positive Bacilli bacteria include *Bifidobacterium* spp., *Lactobacillus* spp., *Lactococcus* spp., *Carnobacterium* spp., *Streptococcus* spp., and *Bacillus* spp.

The term "probiotic composition" refers to a composition that contains a live probiotic microorganism alone, in combination with another microorganism, and/or combined with other ingredients such as e.g., energy sources, pre-biotics, stabilizers, and the like. Probiotic microorganisms are generally known in the art and include such bacteria as lactic acid fermenting (obligative and facultative) bacteria, phototrophic bacteria, and non-pathogenic bacilli, as well as fermenting yeast such as the Saccharomycetaceae. Probiotic compositions are generally known to be useful in ameliorating gut flora, remediating wastewater, treating microbial imbalances in animals and plants, protecting animals, plants, and soil from harmful microbes, and improving food animal and food plant production and yield. Useful probiotic microorganisms can be found listed for example in Probiotic Bacteria: Fundamentals, Therapy, and Technological Aspects, edited by J. Paulo Sousa e Silva, Ana Cristina Freitas, CRC Press, Apr. 2, 2014; and The European Union Register of Feed Additives pursuant to Regulation (EC) No 1831/2003, Annex I: List of additives, available at https://ec.europa.eu/food/sites/food/files/safety/docs/animal-feed-eu-reg-comm_register_feed_additives_1831-03.pdf.

The term "pharmaceutical composition" refers to a preparation of one or more compositions of the invention with additional components such as physiologically suitable carriers and excipients. The purpose of a pharmaceutical composition is to facilitate administration of a composition to a recipient subject.

The term "physiologically acceptable carrier" refers to a carrier or a diluent that does not cause significant irritation to a subject and does not abrogate the biological activity and properties of the administered composition.

The term "excipient" refers to an inert substance added to a pharmaceutical composition to further facilitate administration of a composition. Examples, without limitation, of excipients include calcium carbonate, calcium phosphate, various sugars and types of starch, cellulose derivatives, gelatin, vegetable oils and polyethylene glycols. Techniques for formulation and administration of pharmaceutical compositions are known in the art and may be found in "Remington's Pharmaceutical Sciences," Mack Publishing Co., Easton, Pa., latest edition, which is incorporated herein by reference.

As used herein, "subject" refers to a living organism having a central nervous system. In particular, subjects include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific values (e.g., captive or free specimens of endangered species), or mammals which otherwise have value. Suitable subjects also include: mice, rats, dogs, cats, ungulates such as cattle, swine, sheep, horses, and goats, lagomorphs such as rabbits and hares, other rodents, and primates such as monkeys, chimps, and apes. Subjects may be of any age including new born, adolescence, adult, middle age, or elderly.

As various changes could be made in the above compositions and methods without departing from the scope of the invention, it is intended that all matter contained in the above description and in the Examples given below, shall be interpreted as illustrative and not in a limiting sense.

EXAMPLES

Example 1

Microorganism Consortium Formulation

Probiotic compositions were made as follows according to Table 1. Purified water was added to a mixing tank. Molasses (Brix 80+5%, pH 5.7+0.5, Sucrose 30+5% or Total Sugar of 75+5%) was added to the water in the mixing tank. The water and molasses were mixed at 30 Hz speed and then SDA-3C, 199.9+0.1 Proof, 95+1% Ethanol, 4.75+0.50% IPA was added to the mix along with vinegar (120+1 Titratable Acidity). Next, mineral powder (0.15% Mg (as MgO), 0.6% Fe, 0.15% P (as $P_2O_5$), 3.2% K (as $K_2O$) was added to the mixture. The mixture was pumped into a fermentation tank. A probiotic mix (*Bacillus subtilis, Bifidobacterium animalis, Bifidobacterium bifidum, Bifidobacterium longum, Enterococcus lactis, Enterococcus thermophilus, Lactobacillus acidophilus, Lactobacillus bulgaricus, Lactobacillus casei, Lactobacillus fermentum, Lactobacillus plantarum, Rhodopseudomonas palustris, Rhodopseudomonas sphaeroides,* and *Saccharomyces cerevisiae*) was added into the mixing tank and blended. Then, the probiotic mix was pumped into the fermentation tank. The residue remaining in the mixing tank was rinsed using water and pumped into the fermentation tank. The probiotic mix was fermented for 21 days at a temperature of 38° C. and a pH below 3.6.

TABLE 1

| Formulations | | | | | | | | | |
|---|---|---|---|---|---|---|---|---|---|
| Water (L) | 4968.6 | 4831 | 4581.1 | 4407.2 | 4329 | 4038.6 | 4984 | 4989 | 4713.8 |
| Molasses (L) or Rice bran (kg) | 101.9 | 254.8 | 509.6 | 672 | 764.4 | 1019.2 | 101.9 | 101.9 | 101.9 |
| Mineral Powder (kg) | 25.5 | 10.2 | 5.1 | 16.8 | 2.6 | 38.2 | 10.1 | 5.1 | 25.5 |
| Sea Salt(kg) | 25.5 | 10.2 | 5.1 | 16.8 | 2.6 | 38.2 | 10.1 | 5.1 | 25.5 |
| Probiotic Mix (kg) | 487.3 | 382.2 | 254.8 | 487.3 | 127.4 | 509.6 | 382.2 | 254.8 | 127.4 |
| Water (L) | 4955.9 | 4066.6 | 4071.7 | 4051.3 | 4038.6 | 4560.9 | 4560.9 | 4560.9 | 4530.9 |
| Molasses (L) or Rice bran (kg) | 101.9 | 1019.2 | 1019.2 | 1019.2 | 1019.2 | 509.6 | 509.6 | 509.6 | 509.6 |
| Mineral Powder (kg) | 38.2 | 10.2 | 5.1 | 25.5 | 38.2 | 25.5 | 25.5 | 25.5 | 25.5 |
| Sea Salt(kg) | 38.2 | 10.2 | 5.1 | 25.5 | 38.2 | 25.5 | 25.5 | 25.5 | 25.5 |
| Probiotic Mix (kg) | 51 | 382.2 | 254.8 | 127.4 | 51 | 254.8 | 254.8 | 254.8 | 254.8 |

What is claimed is:

1. A liquid probiotic composition comprising:
   a) a carbon source;
   b) a fermentation product;
   c) about 20,000 to 50,000 cfu/mL of a combination of microorganism species comprising at least five microorganism species selected from the group consisting of:
      i) *Bacillus subtilis,*
      ii) a *Lactobacillus* sp.,
      iii) a *Bifidobacterium* sp.,
      iv) a *Lactococcus* sp., and
      v) *Streptococcus thermophilus*; and
   d) a yeast.

2. The liquid probiotic composition of claim 1, further comprising≥50,000 cfu/mL of a purple non-sulfur bacterium.

3. The liquid probiotic composition of claim 1, wherein said yeast is *Saccharomyces* spp.

4. The liquid probiotic composition of claim 1, wherein the *Bifidobacterium* sp. comprises *Bifidobacterium animalis*, the *Lactobacillus* sp. comprises *Lactobacillus casei* subspecies *rhamnosus*, and the yeast comprises *Saccharomyces cerevisiae.*

5. The liquid probiotic composition of claim 1, wherein said purple non-sulfur bacterium is a *Rhodopseudomonas palustris*, a *Rhodobacter sphaeroides*, or a combination thereof.

6. A method of manufacturing a probiotic composition, said method comprising:
   a) obtaining a fermented product containing a consortium of live lactic acid bacteria comprising *Bacillus subtilis*, a *Lactobacillus* sp., a *Bifidobacterium* sp., a *Lactococcus* sp., and *Streptococcus thermophilus*; and
   b) combining another non-pathogenic gram-positive Bacilli bacterium capable of fermentation and a yeast with said fermented product.

7. A method of manufacturing a probiotic composition, said method comprising obtaining a fermented product containing a consortium of live microorganisms comprising *Bacillus subtilis, Bifidobacterium animalis, Bifidobacterium bifidum, Bifidobacterium longum, Enterococcus lactis, Enterococcus thermophilus, Lactobacillus acidophilus, Lactobacillus bulgaricus, Lactobacillus casei, Lactobacillus fermentum, Lactobacillus plantarum, Rhodopseudomonas palustris, Rhodopseudomonas sphaeroides*, and *Saccharomyces cerevisiae*.

\* \* \* \* \*